(12) United States Patent
Svetliza

(10) Patent No.: US 6,267,752 B1
(45) Date of Patent: Jul. 31, 2001

(54) MULTI-FUNCTIONAL EYELID SPECULUM

(75) Inventor: Eduardo Svetliza, Caesarea (IL)

(73) Assignee: Medibell Medical Vision Technologies, Ltd., Haifa (IL)

( * ) Notice: Subject to any disclaimer, the term of this patent is extended or adjusted under 35 U.S.C. 154(b) by 0 days.

(21) Appl. No.: 09/368,523

(22) Filed: Aug. 5, 1999

(51) Int. Cl.$^7$ .......................... A61M 35/00; A61B 17/02
(52) U.S. Cl. .......................... 604/294; 600/205; 600/236
(58) Field of Search .................................. 604/294, 296, 604/297, 301, 302, 300, 295, 289, 290; 600/184, 205, 208, 210, 235, 236, 201; 606/165

(56) References Cited

U.S. PATENT DOCUMENTS

| | | | |
|---|---|---|---|
| 5,054,906 | * 10/1991 | Lyons, Jr. | 351/205 |
| 5,582,608 | * 12/1996 | Brown | 606/4 |
| 5,695,492 | * 12/1997 | Brown | 606/4 |
| 5,762,606 | * 9/1998 | Minnich | 600/205 |
| 5,971,977 | * 10/1999 | Korenfeld | 606/1 |
| 6,074,343 | * 6/2000 | Nathanson et al. | 600/214 |

* cited by examiner

*Primary Examiner*—Kim M. Lewis
(74) *Attorney, Agent, or Firm*—Edward Langer, Pat. Atty.

(57) ABSTRACT

An eyelid speculum for separation of the eyelids with an automatic system for irrigation and aspiration. In one embodiment, the speculum is provided as a truncated cone-shaped main body with lid retractors extending out of it in the form of a ring, forming an angle appropriate to the curvature of the eye. Hollow rings are provided in the body of the cone with perforated channels for delivering irrigation fluid and for aspiration. Two syringes are provided, each connected by tubing to one of the hollow rings so as to either deliver irrigation or aspirate excess fluid. The irrigation and aspiration rates are controlled by an electronic processor which controls the rates of both activities independently. In another embodiment, the device is further provided with an illumination unit for trans-illumination via the sclera of the interior of the eyeball. The light which reaches the interior of the eyeball through the sclera is diff-use and homogeneous and thus comfortable for the surgeon to work with while not endangering the eye tissue. There is no need for the user to illuminate the eye with the harsh light of the microscope. In yet another embodiment, a second type of illumination unit is added which provides illumination of the anterior segment of the eye from an inclined angle so as produce soft and indirect lighting.

23 Claims, 5 Drawing Sheets

MULTI-FUNCTIONAL EYELID SPECULUM

FIELD OF THE INVENTION

The present invention relates to an eyelid speculum for ophthalmic use, in particular an apparatus which irrigates and aspirates the corneal solutions automatically, and illuminates the interior and exterior of the eye.

BACKGROUND OF THE INVENTION

The eyelid speculum is a well known device in the field of ophthalmology, both for use in diagnostics and in surgery of the anterior and posterior segments of the eye. The purpose of an eyelid speculum is to mechanically retract the eyelids from the surface of the eyeball. Although retraction is necessary for a physician to work, it keeps the eyelids from performing their natural function of lubrication. Therefore, there is a risk of the cornea drying out. Current practice requires an assistant to irrigate the area manually every few moments, so as to provide artificial lubrication to neutralize the drying process caused by the speculum. Long-term non-lubrication of the eye when the speculum is in place may cause injury to the cornea, affecting its transparency and integrity.

There exist speculums with irrigation/aspiration features (Storz Ophthalmic Inc., U.S. and Moria Co., France), however these are provided in a manual form, requiring the physician to push or pull on the plunger of the syringe provided as needed. This is not practical as the physician's hands are required for the surgery and constant removal from the site is counter-productive. Therefore, there is no added benefit to this speculum, as a second set of hands is still necessary to make it useful.

Additionally, the physician working with the speculum requires an illumination source to illuminate the work area. The ophthalmic surgeon operates through use of a microscope with an illumination source which delivers coaxial light. The coaxial light source provides a high level of illumination which has a phototoxic effect on the eye tissue. It is necessary to use a combination of filters or light-dimming techniques to reduce these effects. Even so, the surgeon uses only a portion of the light which reaches the anterior eye tissue and the remaining, unnecessary light penetrates the eye and is absorbed by the retina. The intensity of the unnecessary light causes phototoxicity, damaging the photoreceptors on the retina. Research has shown that not only are the rods and cones affected, but the excess light on the retina may cause burns on the different layers of the retinal tissue. In addition, the intense light is uncomfortable for the patient and may cause excess tearing.

In certain techniques, such as vitrectomny and endophotocoagulation, for the treatment of advanced retinal disorders, different types of miniature probes are introduced into the eye, by way of example, for cutting membranes, aspiration of residues, oil and gas infusions and laser photocoagulation therapy. Included in these probes is an illumination probe which functions in illuminating that small portion of the retina which is being treated. Consequently, a small portion of the retina receives a concentrated quantity of light delivered by the probe, which is connected to a strong light source. This type of light source also causes the phototoxic effect reported above.

U.S. Pat. No. 5,054,906 to Lyons discloses an indirectly illuminating ophthalmalogical speculum which is primarily suited for external illumination of the cornea in ophthalmogical procedures on the surface of the eye. The speculum is provided as a conventional eyelid speculum with two fiber optics mounted thereon. These fiber optics do not provide a circumferential or constant homogeneous illumination of the eye. Additionally, the Lyons speculum does not provide for trans-illumination of the eyeball, for use in cases where the physician must view the interior of the eye, but rather is designed for use on the surface of the eyeball.

U.S. Pat. Nos. 5,582,608 and 5,695,492 to Brown describe an embodiment with a ring illumination for hand-held use, or to be attached to a support. The device must be used in combination with an eyelid speculum, or the eyelids will occlude the field under observation. Brown provides interior trans-illumination for the purpose of retroillumination, i.e. for the physician to look at the light returning through the lens to see the pathology of the lens. However, the Brown patent does not provide for trans-illumination for the pupose of examining the retinal pathology. Examination of the retina requires a stronger light intensity, potentially causing damage to the retina during long-term radiation. The Brown patent does not allow for this use, or make accommodation for minimizing the damage of a light which is introduced conventionally through the pupil of the eye.

Therefore, it would be desirable to provide an eyelid speculum which would automatically irrigate and aspirate the eye surface, while optionally providing a light source which would provide homogeneous, constant, well-distributed illumination of either the interior or exterior of the eyeball as needed while not causing phototoxic effects on the eye tissue and would provide an illumination system independent of the optical system.

SUMMARY OF THE INVENTION

Accordingly, it is a broad object of the present invention to overcome the problems of the prior art and provide a multi-functional speculum which irrigates and aspirates the eyeball surface, and optionally provides a safe and homogeneous light source for illumination of both the interior and the exterior of the eye as needed, while not causing phototoxic effects on the eye tissue.

In accordance with a preferred embodiment of the present invention, there is provided a multi-functional eyelid speculum comprising:

a main body defining a perimeter of a work area;
an eyelid retractor extending from said main body, comprising a substantially flat ring fitting the angle of curvature of an eye, for separating a pair of eyelids so as not to obstruct access to the eye in said work area; and
means for automatically irrigating and aspirating an eye surface mounted on said main body at at least one point on said main body perimeter.

In a preferred embodiment of the invention there is provided an eyelid speculum for separation of the eyelids with an automatic system for irrigation and aspiration. The speculum is provided, by way of example, as a truncated cone-shaped main body with lid retractors extending out of it in the form of a ring, forming an angle appropriate to the curvature of the eye. Hollow rings are provided in the body of the cone with perforated channels for delivering irrigation fluid and for aspiration. Two syringes are provided, each connected by tubing to one of the hollow rings so as to either deliver irrigation or aspirate excess fluid. Each syringe is connected to a small motor by a screw wherein the direction of the motor rotor determines the intake and output of the syringe's piston. The irrigation and aspiration rates are controlled by an electronic processor which controls the rates of both activities independently.

A simplified version of this embodiment may be provided, in which one syringe, one tube and one hollow ring are used both for irrigation and for aspiration, as needed. Alternatively, two syringes may lead into a common tube and hollow ring allowing irrigation from one syringe and aspiration of material into a separate syringe.

In another preferred embodiment, the device is further provided with an illumination unit for trans-illumination via the sclera of the interior of the eyeball. The light which reaches the interior of the eyeball through the sclera is diffuse and homogeneous and thus comfortable for the surgeon to work with while not endangering the eye tissue. There is no need for the user to illuminate the eye with the harsh light of the microscope.

The illumination unit is provided as a light source connected to a plurality of light guiding elements which are circumferentially arranged in a hollow ring in the main body of the speculum. In one design, a single light source controls all of the light elements in the ring. In another variation, at least two light sources are provided, separating control of the light supplied to the light elements on two opposite sides of the eyeball, providing for lighting from only one side or for increased intensity on one side or the other.

In yet another embodiment, a second type of illumination unit is added which provides illumination of the anterior segment of the eye from an inclined angle so as produce soft and indirect lighting.

In a further embodiment, there is provided a pair of tabs for holding the eyelids apart, these tabs defining a space through which the tubing and optical fiber channel reach the main body of the device. These tabs provide for a construction in which the eyelids closing on the device secure the device in place with no need for the user to hold it. Light is provided from the side of the main body by the optical fiber channel, for illumination of the retina. The tubing provides for irrigation and aspiration of the area, and may be bifurcated so as to allow separate irrigation and aspiration lines. The automatic control of irrigation and aspiration is provided in the same way as in previous embodiments.

In a still further embodiment, the light sources are provided directly on the main body, so as to provide maximal efficiency of light transmittal. Irrigation and aspiration may be achieved as in any of the above embodiments. The light sources are doubly insulated to prevent any contact of the irrigation solution with the electricity. The light from the light sources is transmitted through a light conducting channel to a light transmitting surface and may be provided with a disposable lower section, in which the light conducting channel and the transmitting surface are provided as a one-use disposable unit for maintaining sterility. The disposable unit is reversibly attached to the main body containing the light sources.

By lengthening the cone shaped main-body, the ring which comes in contact with the eye is of a smaller diameter, and thus suitable for use in newborns.

Other features and advantages of the invention will become apparent from the following drawings and descriptions.

BRIEF DESCRIPTION OF THE DRAWINGS

For a better understanding of the invention with regard to the embodiments thereof, reference is made to the accompanying drawings, in which like numerals designate corresponding elements or sections throughout and in which.

DETAILED DESCRIPTION OF THE PRESENT INVENTION

Figure 1:
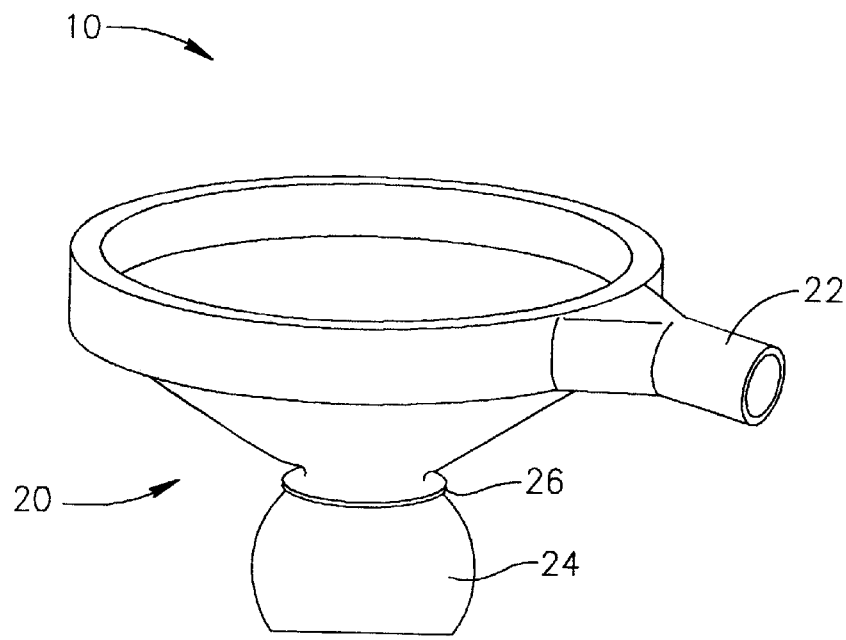
FIG. 1 is a perspective drawing of a preferred embodiment of a speculum constructed and operated in accordance with the present invention.

Referring now to FIG. 1, there is shown a perspective drawing of a preferred embodiment of a speculum 10 constructed and operated according to the present invention, featuring irrigation and aspiration systems described further herein. Speculum 10 is composed of main body 20 and sheath 22. Main body 20 is, by way of example, substantially truncated cone-shaped, with the narrow end of the cone sitting on the surface of eyeball 24 when in use, the perimeter of the cone defining the work area. Extending from main body 20 is lid retractor ring 26 which keeps the eyelids of the patient away from the working area. Main body 20 may be provided with an extension of the cone-shaped main body providing a lid retractor ring 26 of smaller diameter, for use with infants (not shown).

Figure 2:
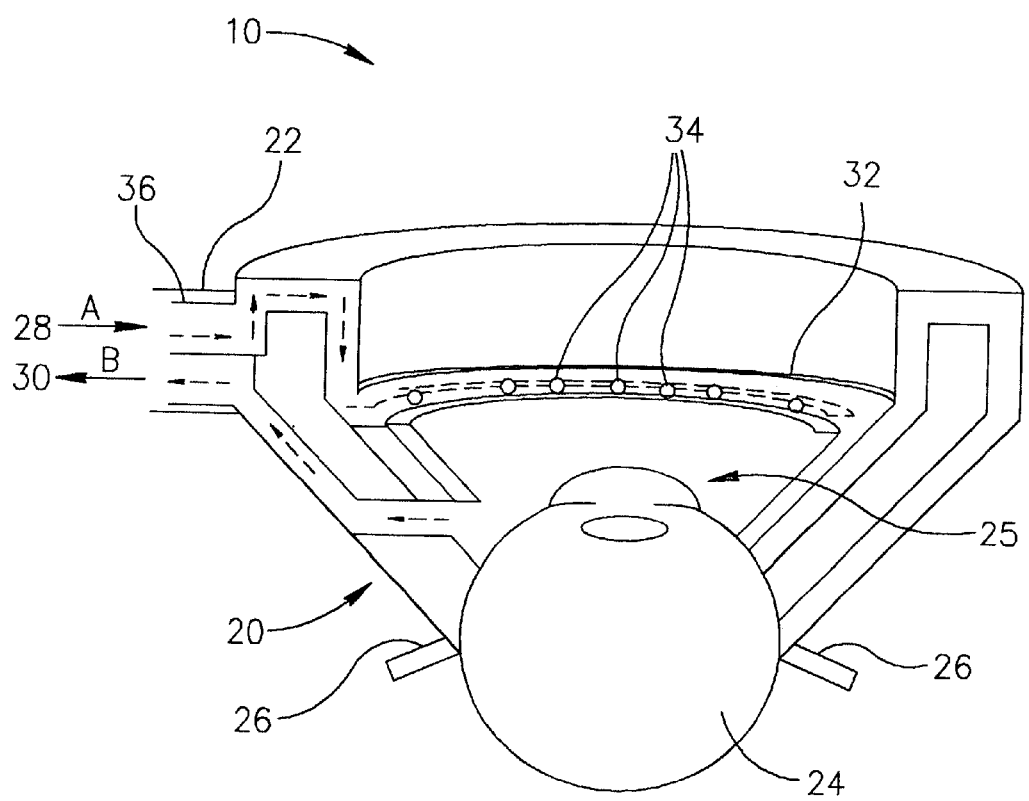
FIG. 2 is a cross-sectional drawing of the speculum showing the irrigation and aspiration systems.

In FIG. 2, speculum 10 is shown in cross-section, showing the workings of the irrigation and aspiration systems. In a preferred embodiment, sheath 22 contains tubing 28 through which the irrigation solution flows, and tubing 30 through which the aspirated fluid is extracted. Irrigation tubing 28 leads to hollow ring 32, in the direction of arrow "A", and is supplied with at least one, and preferably a plurality of small openings 34, located in a distributed fashion around the 360° ring, through which the irrigation solution is sprayed onto anterior surface 25 of eyeball 24. The irrigation solution can be supplied as any physiological solution. Aspiration tubing 30 leads from surface 25 of eyeball 24, where excess irrigation solution, biological fluids and extraneous matter are accumulated, and removes this material in the direction of arrow "B".

Figure 3:
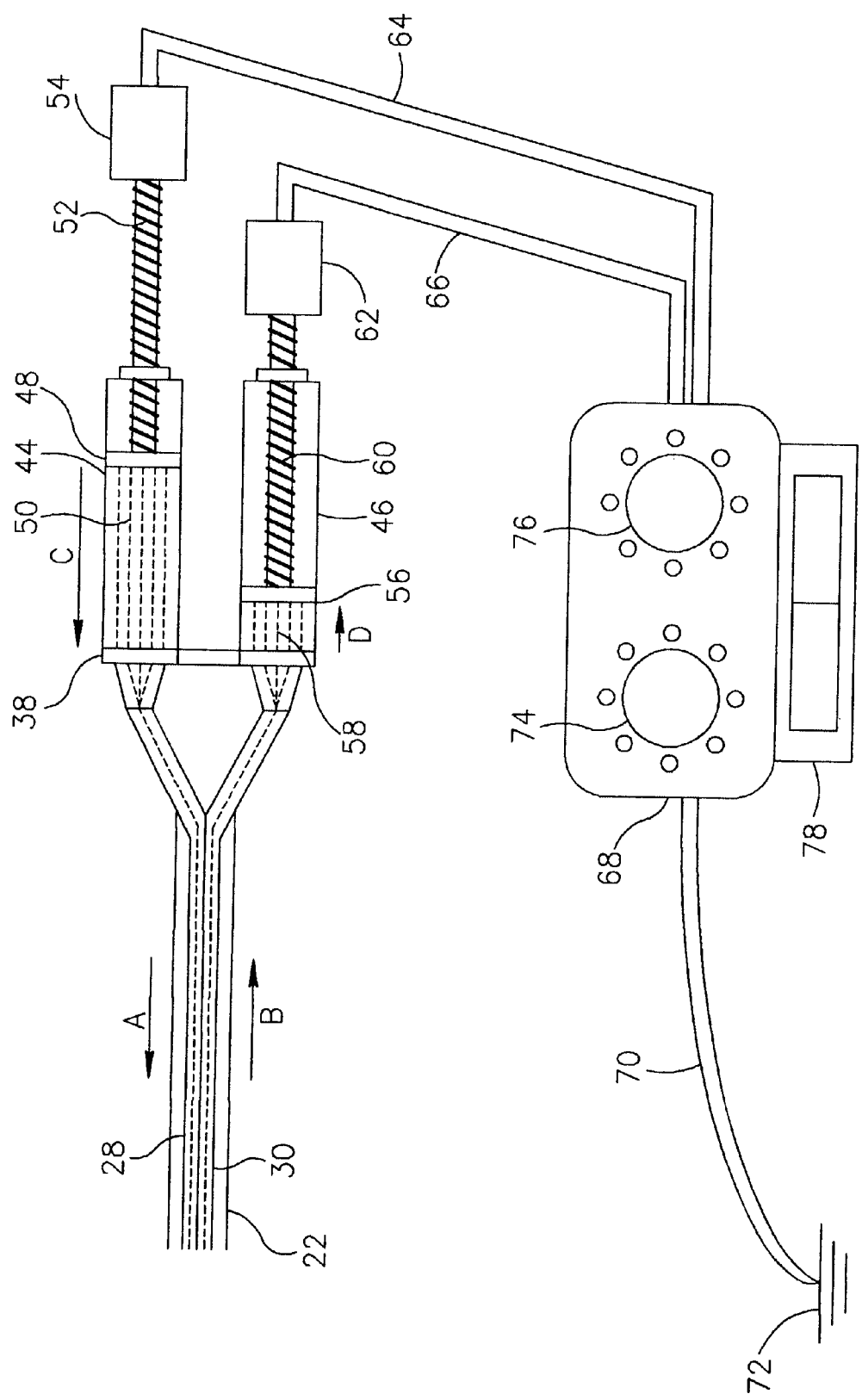
FIG. 3 is an illustration of the automatic irrigation and aspiration system.

In FIG. 3 there is shown an illustration of a preferred embodiment of the irrigation and aspiration system. Sheath 22 leads from the speculum to the irrigation and aspiration system. Sheath 22 is bifurcated providing irrigation through one set of tubing 28 and aspiration through a second set of tubing 30, as seen in FIG. 2. Tubings 28 and 30 lead into support 38. Two syringes 44 and 46 extend from support 38 in communication with irrigation tubing 28 and aspiration tubing 30, respectively. Irrigation syringe 44 is supplied with piston 48 which moves in the direction of arrow "C" so as to expel physiological solution 50 from the body of syringe 44. Piston 48 is controlled by screw 52, which is driven into rotational motion by motor 54.

Similarly, syringe 46 contains piston 56 which moves in the direction of arrow "D", so as to aspirate fluid 58. Piston 56 is controlled by screw 60, which is driven into rotational motion by motor 62.

The performance of motors 54 and 62 is similar except that motor 54 drives screw 52 so as to expel fluid and motor 62 drives screw 60 so as to draw in fluid. DC electrical power activates motors 54 and 62 through wires 64 and 66, respectively. Wires 64 and 66 are connected to a transformer located in control box 68. Control box 68 is powered with AC current received through wire 70 which is connected to a power source 72. It will be appreciated that power source 72 may be provided by an electrical network or through batteries for portable operation. Knobs 74 and 76 regulate the rates of the activity of irrigation and aspiration by syringes 44 and 46, respectively. The rate of the control of knobs 74 and 76 is displayed digitally on split LCD screen 78, for better adjustment by the operator. In this manner, a completely automatic mode of operation is provided.

Additionally, knobs 74 and 76 may be manually depressed by the operator so as to close the circuit of either motor 54 or 62, respectively, providing an electrical pulse for semi-automatic operation of the device. The manual circuit is connected parallel to the automatic circuit. Thus, the operator has full manual or automatic control of the irrigation and aspiration activity.

Alternatively, the speculum can be provided with an irrigation and aspiration system in which sheath 22 is not bifurcated, and fluid for irrigation and from aspiration both flow through a single tubing, in response to the action of motors 54 and 62 on pistons 48 and 56, respectively. In yet another embodiment, the speculum can be provided with only one syringe connected to the single tubing, with movement of the syringe piston being accomplished by one motor moving the piston either to expel or take in fluid as necessary. This may be achieved by changing the polarity of the DC electrical power source.

Figure 4:
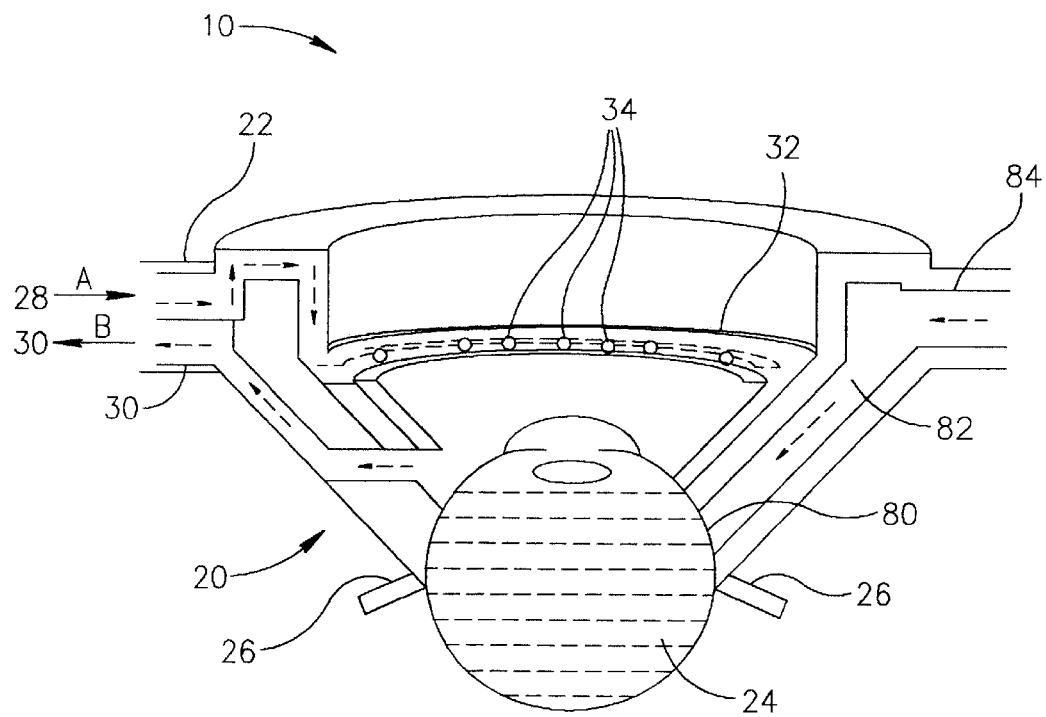
FIG. 4 is a cross-sectional drawing of the speculum with an illumination ring.

Referring now to FIG. 4, there is shown a cross-section of speculum 10 with the addition of illumination ring 80. Illumination ring 80 is preferably positioned on the bottom surface of main body 20 so as to be in direct contact with the sclera of eyeball 24. Light elements 82 enter main body 20 through optical fiber channel 84 and are distributed radially around illumination ring 80 to provide illumination through the sclera of eyeball 24. The radial distribution allows homogeneous light to the retina due to the equal circular dispersion of the intensity of the light and the diffusion effect on the rays of light caused by the sclera and other internal layers. The direct contact of speculum 10 with the sclera prevents the escape of light and thus, most of the intensity of the light transmitted by the optical fibers is absorbed and transmitted by the sclera to the interior of the eye. of speculum 10, through optical fiber channel 84 to at least one optical fiber 96 so as to illuminate the retina of the eye. There is no provision for illumination of the anterior of the eye in this embodiment. Optical fiber channel 84 and sheath 22 enter main body 20 through the side so as not to interfere with retractor tabs 94. Sheath 22 may be bifurcated to provide separate lines for irrigation and aspiration. Automatic and manual control may be provided as in previous embodiments. The irrigation solution reaches the work area through small openings 98 which communicate with sheath 22. Aspiration is achieved through perforations in lid retractor ring 26 which communicate with sheath 22 (not shown). This embodiment allows for more maneuverability for the user and provides for construction of a smaller device. This retractor construction, in combination with its smaller size, causes the eyelids to adequately hold the device in place, without the user holding it.

Figure 8A:
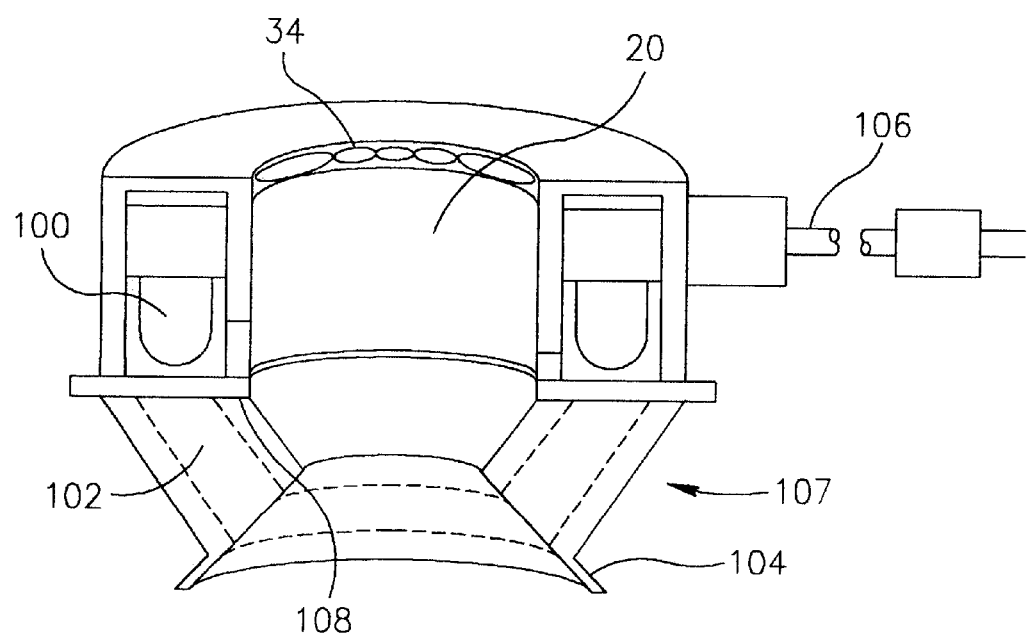
FIGS. 8a–b are, respectively, a cross-sectional drawing and a bottom view of another alternative embodiment of a speculum in which the light sources are provided within the main body and a disposable section is provided.

In FIG. 8a there is shown an alternative embodiment of the speculum of the present invention. Unlike previous embodiments which have used fiber optics to bring the light to speculum 10, in this embodiment the light source is provided directly in main body 20 of speculum 10, so as to provide the most efficient light transmittal.

The use of fiber optics, as in previous embodiments, may result in a light loss of up to 50%, along the length of the fiber. At least one light source 100 is provided, and preferentially a plurality of light sources 100 are provided in a circumferential arrangement around main body 20. Light is transmitted along light conducting channel 102 to light transmitting surface 104. Light transmitting surface 104 rests on the sclera of the eye at an angle appropriate to the eyeball curvature, so that light transmitted through light transmitting surface 104 transilluminates the eye. Electricity reaches light sources 100

In another embodiment, light elements 82 may be provided in two or more bundles, each with its own control, allowing for preferential lighting of one or more areas of the eye. This can be instrumental in diagnosis of various pathologies of the eye, including tumor growth. Additionally, the light may be provided at more than one wavelength, and the light elements of each wavelength may be individually controlled, providing light of different colors for preferential imaging and processing, for example, RGB (red, green, blue) color imaging. Using appropriate light excitation wavelengths the device may be used for angiography.

Figure 5:
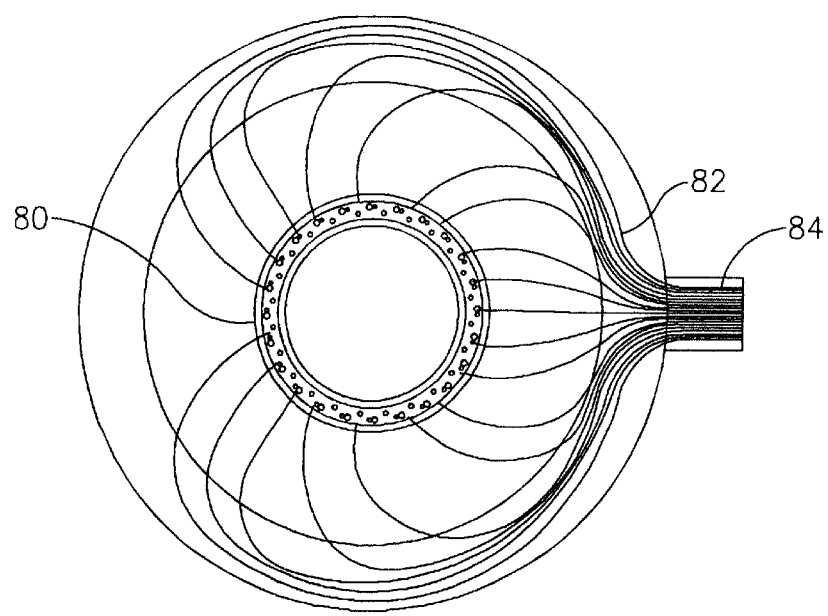
FIG. 5 is an illustration of the radial distribution of the light elements supplied to the illumination ring for illumination of the interior of the eyeball.

FIG. 5 illustrates the radial distribution of fiber optic light elements 82 in an overhead view of illumination ring 80.

Figure 6:
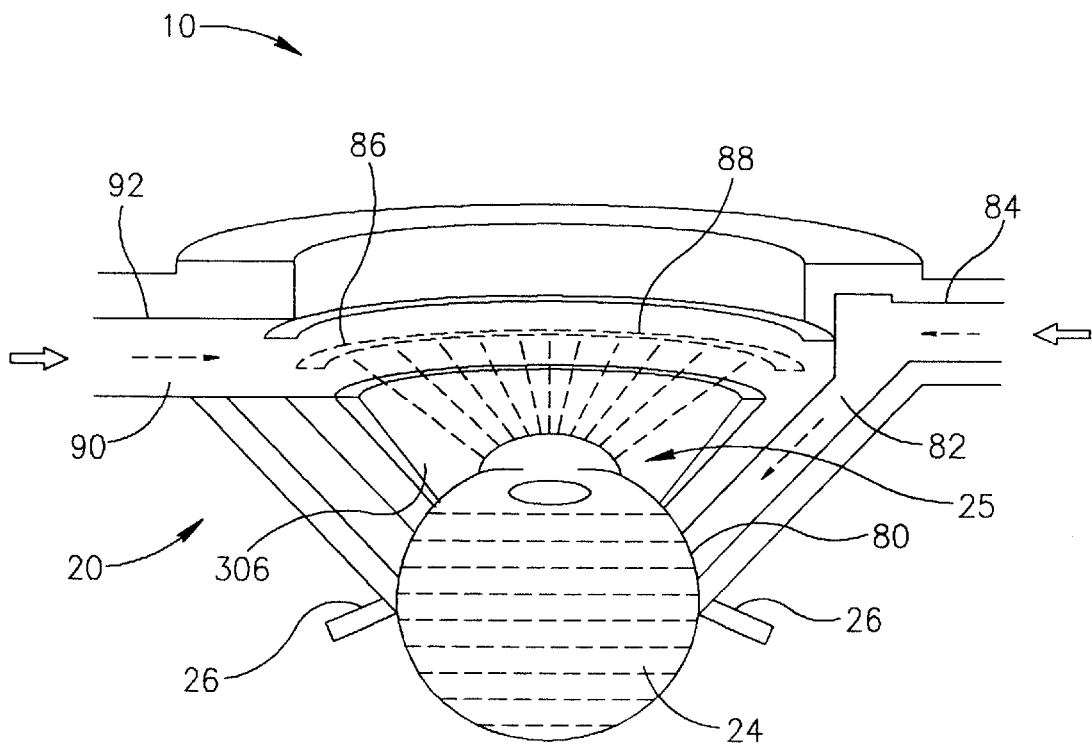
FIG. 6 is a cross-sectional drawing of the speculum provided with a dual illuminator device to illuminate both the interior and anterior of the eye.

As shown in FIG. 6, the speculum of the present invention may be provided with a dual illumination device which allows illumination of both the interior and exterior of the eye. As shown, the speculum is provided with illumination ring 80 as described in FIG. 4 and is additionally provided with a second illumination ring 86 which is positioned in hollow ring 88 provided in main body 20. Illumination ring 86 is provided with light elements 90 through optical fiber channel 92. Light elements 90 are radially distributed through illumination ring 86 and produce light at an angle appropriate to the curvature of the corneal surface. Thus, light is provided on anterior surface 25 of eyeball 24. It will be appreciated that the irrigation and aspiration systems described in FIGS. 2 and 3 are present, but are not shown here.

Figure 7:
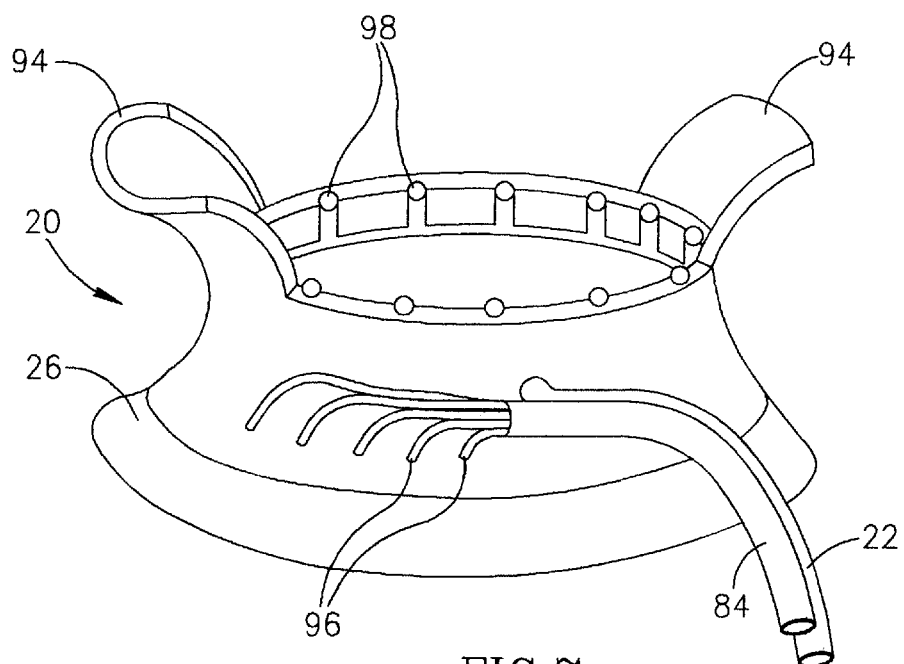
FIG. 7 is a perspective drawing of an alternative embodiment of the speculum of the present invention.

An alternative embodiment of the present invention is shown in FIG. 7. In this embodiment, speculum 10 has main body 20 provided with lid retractor ring 26 and outwardly extending retractor tabs 94. In this embodiment, light is provided from one side through electrical cable 106 which connects to a power source. It will be understood that any of the above-mentioned irrigation and aspiration systems may be used in combination with this embodiment. Light sources 100 are doubly insulated so as to ensure that there is no danger to the patient from the combination of the electricity supplied to light sources 100 and the irrigation solution.

Main body 20 is optionally provided with disposable section 107 for single use, so as to supply each patient with a sterile, unused device in contact with the eye surface. Included in disposable section 107 are light conducting channel 102 and light transmitting surface 104. Disposable section 107 is reversibly attachable by attachment means 108, by way of example, a screw system or a bayonet system. As light source 100 is entirely included in the main body, disposable section 107 may be made of low cost materials such as acrylic so as to keep the unit cost economical. It will be understood by those skilled in the art, that previous embodiments such as those in which fiber optics are used may be adapted to be provided with a disposable section 107 by providing a channel 102 at the terminus of the fiber optics through which the light from the fiber optics may be transmitted and a light transmitting surface 104 which transmits light to eye surface 25.

Figure 8B:
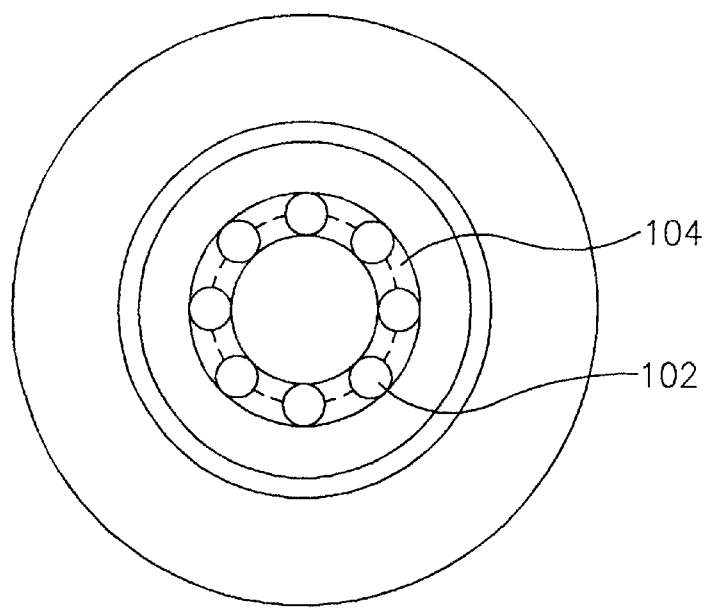

FIG. 8b is a bottom view of speculum 10 where the ends of channel 102 are seen in cross-section through light transmitting surface 104.

Thus, there is provided a multi-functional speculum which automatically irrigates and aspirates the eye surface and optionally provides a safe and homogeneous light source for illumination of the interior and exterior of the eye as needed without causing phototoxic effects on the eye tissue. The speculum can be adapted for use in newborns. The light sources may be provided at predetermined wavelengths to allow for varied uses, such as angiography and color imaging.

Having described the invention with regard to certain specific embodiments thereof, it is to be understood that the description is not meant as a limitation, since further modifications may now suggest themselves to those skilled in the art, and it is intended to cover such modifications as fall within the scope of the appended claims.

What is claimed is:

1. A multi-functional eyelid speculum comprising:
    a main body defining a perimeter of a work area;
    an eyelid retractor extending from said main body, comprising a substantially flat ring fitting the angle of curvature of an eye, for separating a pair of eyelids so as not to obstruct access to the eye in said work area; and
    means for automatically irrigating and aspirating an eye surface mounted on said main body at at least one point on said main body perimeter.

2. The speculum of claim 1 wherein said main body is substantially truncated cone-shaped.

3. The speculum of claim 1 wherein said automatic irrigation and aspiration means further comprises a hollow ring formed in said main body for delivering irrigation solution to the surface of an eye, said hollow ring being formed with at least one small opening providing exit for said irrigation solution from said hollow ring to the surface of an eye.

4. The speculum of claim 1 further comprising at least two retractor tabs for holding a pair of eyelids open, said retractor tabs defining a space through which said means for automatically irrigating and aspirating reach said main body.

5. The speculum of claim 4 further comprising an indirect illumination unit, illuminating an eye through the sclera portion of the eye.

6. The speculum of claim 3 wherein said means for automatically irrigating and aspirating comprises:
    a first syringe;
    means for automatic control of rates of intake and output of said syringe; and
    tubing communicating between said syringe and said main body.

7. The speculum of claim 6 further comprising a second syringe, said first syringe being used for irrigation and said second syringe being used for aspiration through said tubing.

8. The speculum of claim 3 wherein said means for automatically irrigating and aspirating comprises:
    a first syringe for irrigation;
    a second syringe for aspiration;
    means for automatic control of rates of output of said first syringe and intake of said second syringe; and
    a first and second tubing for communicating between said first and second syringes, respectively, and said main body.

9. The speculum of claim 6 wherein said means for automatic control of rates are provided as motorized means for adjusting said irrigation and aspiration rates.

10. The speculum of claim 8 wherein said motorized means are provided with electronic controls.

11. The speculum of claim 10 wherein said motorized means are powered by a reversible polarity DC source for reversing the motion of said motorized means.

12. The speculum of claim 9 wherein said control means is further provided with a manual control means in addition to said automatic control means.

13. The speculum of claim 1 further provided with an illumination unit.

14. The illumination unit of claim 13 wherein said illumination unit is an indirect illumination unit, illuminating an eye through the sclera portion of the eye.

15. The speculum of claim 1 further comprising a hollow ring formed in said main body for providing illumination to the surface of an eye.

16. The speculum of claim 13 wherein said illumination unit comprises a light source connected to a plurality of light guiding elements, said light guiding elements being mounted on the periphery of "said hollow ring" in said main body.

17. The speculum of claim 16 wherein said light guiding elements are provided as fiber optics.

18. The speculum of claim 16 comprising two separately controlled light sources, each connected to a portion of said plurality of light guiding elements.

19. The speculum of claim 13 wherein said illumination unit provides light having at least one pre-determined wavelength.

20. The speculum of claim 14 further comprising a second illumination unit for providing illumination of the surface of an eye.

21. The speculum of claim 13 wherein said illumination unit is comprised of a light source mounted on the main body, and further comprising a channel and a light transmitting surface, light from said light source being transmitted through said channel to said light transmitting surface onto the eye surface.

22. The speculum of claim 21 wherein said main body is provided with a reversibly attachable disposable unit, said disposable unit comprising:
    attachment means for attaching said disposable unit to said main body;
    said channel; and
    said light transmitting surface.

23. The speculum of claim 1 further comprising an extension ring to said main body provided with a small diameter for use with infants.

* * * * *